United States Patent
Smith et al.

(10) Patent No.: US 9,709,534 B2
(45) Date of Patent: Jul. 18, 2017

(54) ULTRASONIC MEASUREMENT

(71) Applicant: The Lubrizol Corporation, Wickliffe, OH (US)

(72) Inventors: Oliver Smith, University Heights, OH (US); Michael R. Sutton, Matlock (GB)

(73) Assignee: The Lubrizol Corporation, Wickliffe, OH (US)

( * ) Notice: Subject to any disclaimer, the term of this patent is extended or adjusted under 35 U.S.C. 154(b) by 228 days.

(21) Appl. No.: 14/388,840

(22) PCT Filed: Mar. 13, 2013

(86) PCT No.: PCT/US2013/030727
§ 371 (c)(1),
(2) Date: Sep. 29, 2014

(87) PCT Pub. No.: WO2013/148179
PCT Pub. Date: Oct. 3, 2013

(65) Prior Publication Data
US 2015/0053005 A1 Feb. 26, 2015

Related U.S. Application Data

(60) Provisional application No. 61/617,117, filed on Mar. 29, 2012.

(51) Int. Cl.
*G01N 29/42* (2006.01)
*G01N 29/04* (2006.01)
(Continued)

(52) U.S. Cl.
CPC ......... *G01N 29/4445* (2013.01); *G01N 29/04* (2013.01); *G01N 29/043* (2013.01);
(Continued)

(58) Field of Classification Search
CPC .... G01N 29/04; G01N 29/4409; G01N 29/46; G01N 29/043; G01N 29/42; G01N 29/4445; G01N 2291/102; G01N 2291/044
(Continued)

(56) References Cited

U.S. PATENT DOCUMENTS 5,121,629 A * 6/1992 Alba ............... G01N 15/02
73/602
5,408,881 A 4/1995 Piche et al.
(Continued)

FOREIGN PATENT DOCUMENTS

GB 2085591 A 4/1982

*Primary Examiner* — J M Saint Surin
(74) *Attorney, Agent, or Firm* — Christopher D. Hilker; David M. Shold; Teresan W. Gilbert

(57) ABSTRACT

Ultrasonic measurement apparatus 10 includes a transmitter 14 to transmit an ultrasonic signal 16 into an item 12. A receiver 18 receives echoes 20 from the item 12. The apparatus 10 measures the frequency spectrum of the echo 20 and makes a comparison with another frequency spectrum to extract information relating to a change in the item 12. For example, the item 12 may wear during use. A comparison of the frequency spectrum, with previous frequency spectra, allows changes of dimension of the item 12 to be identified. Changes in amplitudes of the frequency spectrum allow changes in roughness to be detected.

17 Claims, 4 Drawing Sheets

Figure 1:
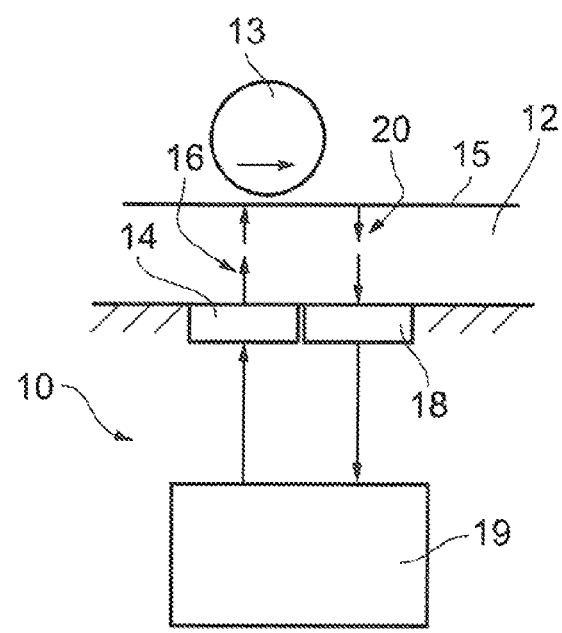

(51) Int. Cl.
*G01N 29/46* (2006.01)
*G01N 29/44* (2006.01)

(52) U.S. Cl.
CPC ......... *G01N 29/42* (2013.01); *G01N 29/4409* (2013.01); *G01N 29/46* (2013.01); *G01N 2291/044* (2013.01); *G01N 2291/102* (2013.01)

(58) Field of Classification Search
USPC .................................................. 73/579, 659
See application file for complete search history.

(56) References Cited

U.S. PATENT DOCUMENTS

| | | | | |
|---|---|---|---|---|
| 7,353,709 | B2* | 4/2008 | Kruger | G01N 29/11 73/599 |
| 8,175,820 | B2* | 5/2012 | Hatanaka | G01N 29/0618 702/35 |
| 2004/0153268 | A1* | 8/2004 | Volkel | G01H 1/003 702/75 |
| 2007/0006651 | A1* | 1/2007 | Kruger | G01N 29/11 73/579 |
| 2008/0282805 | A1* | 11/2008 | Onodera | G01N 29/043 73/629 |
| 2009/0143681 | A1 | 6/2009 | Jurvelin et al. | |
| 2010/0145639 | A1* | 6/2010 | Fu | G01H 1/003 702/56 |

\* cited by examiner

ULTRASONIC MEASUREMENT

The present invention relates to ultrasonic measurement, and particularly, but not exclusively, to apparatus and methods for ultrasonic measurement of changes in an item. Changes may be as a result of wear.

In many circumstances, it is useful to be able to identify changes in an item, such as the effects of wear. For example, an item that has regular contact with another item during use might change in dimensions or roughness over time, as it is worn away by the contact. Wear may also occur without contact, for example through corrosive wear. Identifying wear of an item can be important in calculating the expected life of the item, so that the item can be replaced before it fails or causes damage. Understanding the effects of wear is particularly important in machine components such as vehicle engine components or bearings. Identifying wear can also be useful in testing the performance of an associated system, such as a lubrication system.

Examples of the present invention provide a method of ultrasonic measurement, the method comprising the steps of:
causing an ultrasonic signal to be transmitted into an item;
causing an echo of the transmitted ultrasonic signal to be received from the item;
measuring the frequency spectrum of the echo; and
undertaking a comparison with another frequency spectrum to extract information relating to a change in the item.

Frequency spectra may be repeatedly measured for comparison as aforesaid to extract information relating to progressive change in the item.

The change may relate to a dimension of the item. The change may relate to wear. The change may relate to wear at a surface of the item. Information may be extracted by comparing the shapes of the frequency spectra.

The change may relate to roughness at the surface of the item. Information may be extracted by comparing amplitudes of the frequency spectra. Peak amplitudes may be compared.

The transmitted ultrasound signal may include a spectrum of frequencies.

The frequency spectrum of the echo may be obtained by a Fast Fourier Transform (FFT) analysis. The said another frequency spectrum may be a frequency spectrum measured previously from the same item. The said another frequency spectra may be a frequency spectrum derived by a mathematical model of the change. The mathematical model may be based on the geometry and material properties of the item.

The steps of transmitting and receiving may be repeated to measure a plurality of frequency spectra of echoes, the plurality of spectra being combined for comparison with the said another spectrum.

The item may comprise regions of different material properties which meet at interfaces from which echoes are reflected. The item may have a surface layer of material, the dimensions of the surface layer changing with use of the item. The surface layer may wear during use. The roughness of the surface layer may change during use.

The item may be a bearing. The transmitted signal may include ultrasound at a frequency between 0.5 MHz and 100 MHz, such as 10 MHz.

Examples of the present invention also provide apparatus for ultrasonic measurement of an item, comprising:
a transmitter operable to transmit an ultrasonic signal into the item;
a receiver operable to receive from the item an echo of the transmitted signal; and
the apparatus being operable to measure the frequency spectrum of the echo and to make a comparison with another frequency spectrum to extract information relating to a change in the item.

The apparatus may be operable in accordance with any of the methods set out above.

Figure 2A:
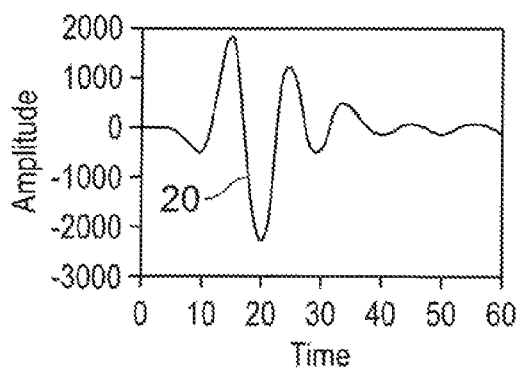
Figure 3:
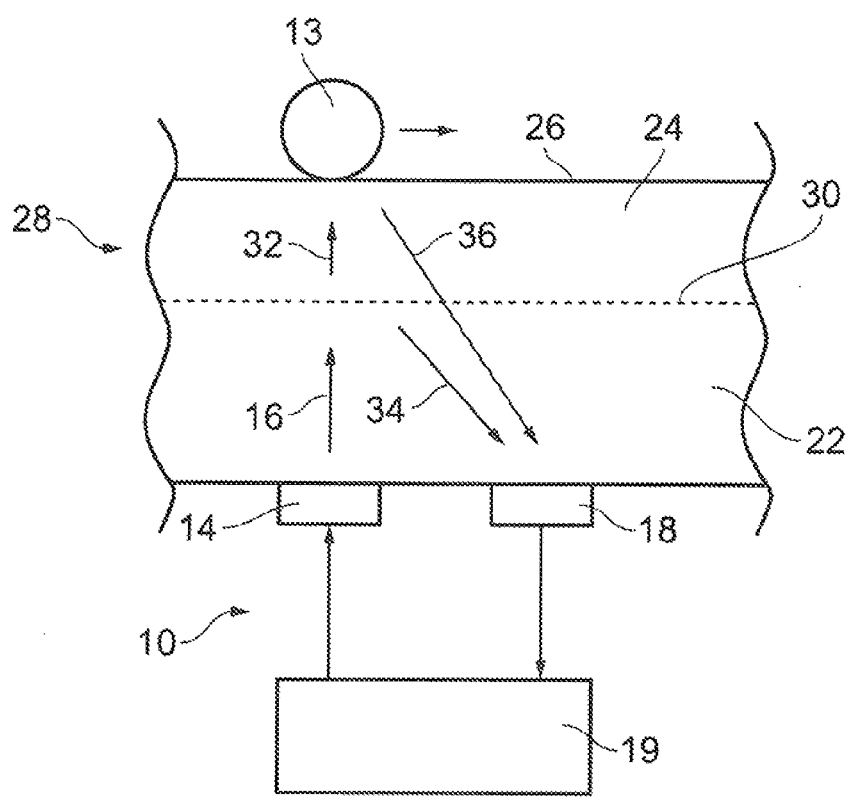
Figure 4A:
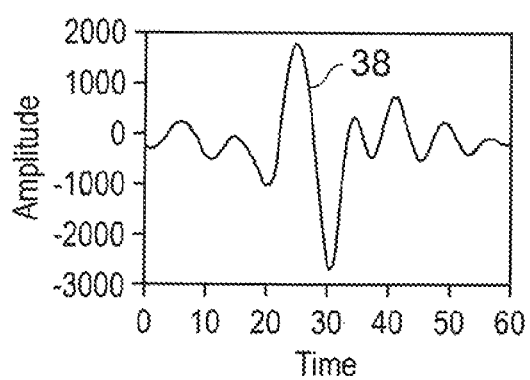
Figure 5A:
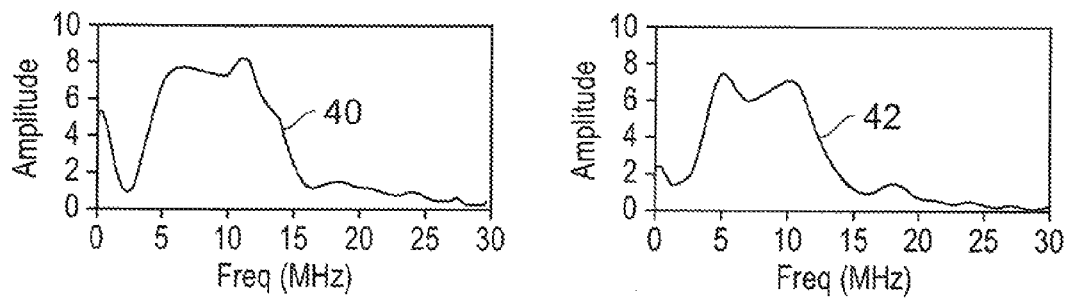
Figure 5B:
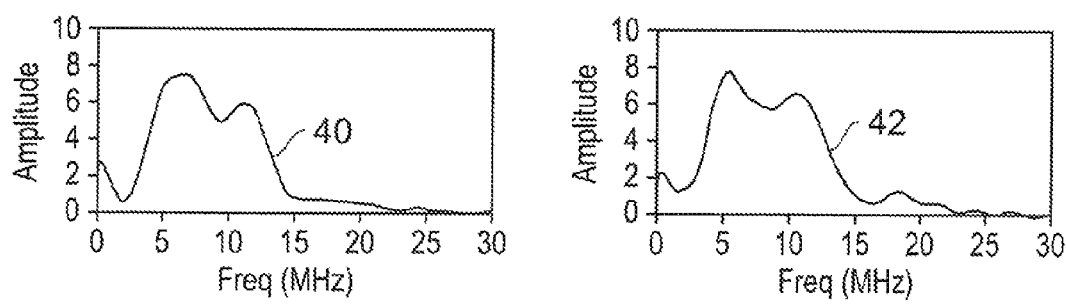
Figure 5C:
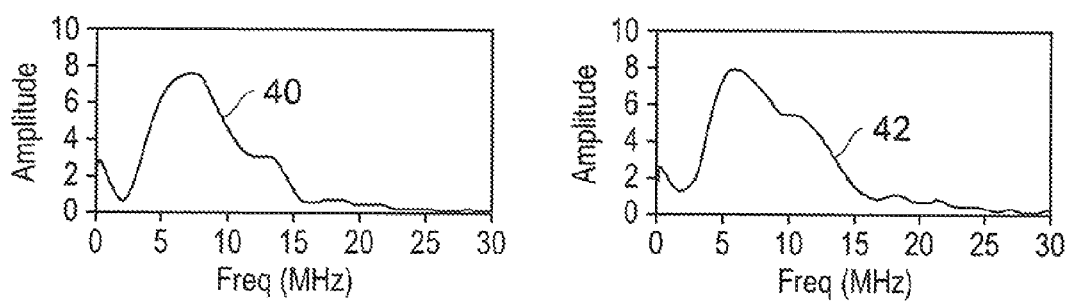
Figure 6:
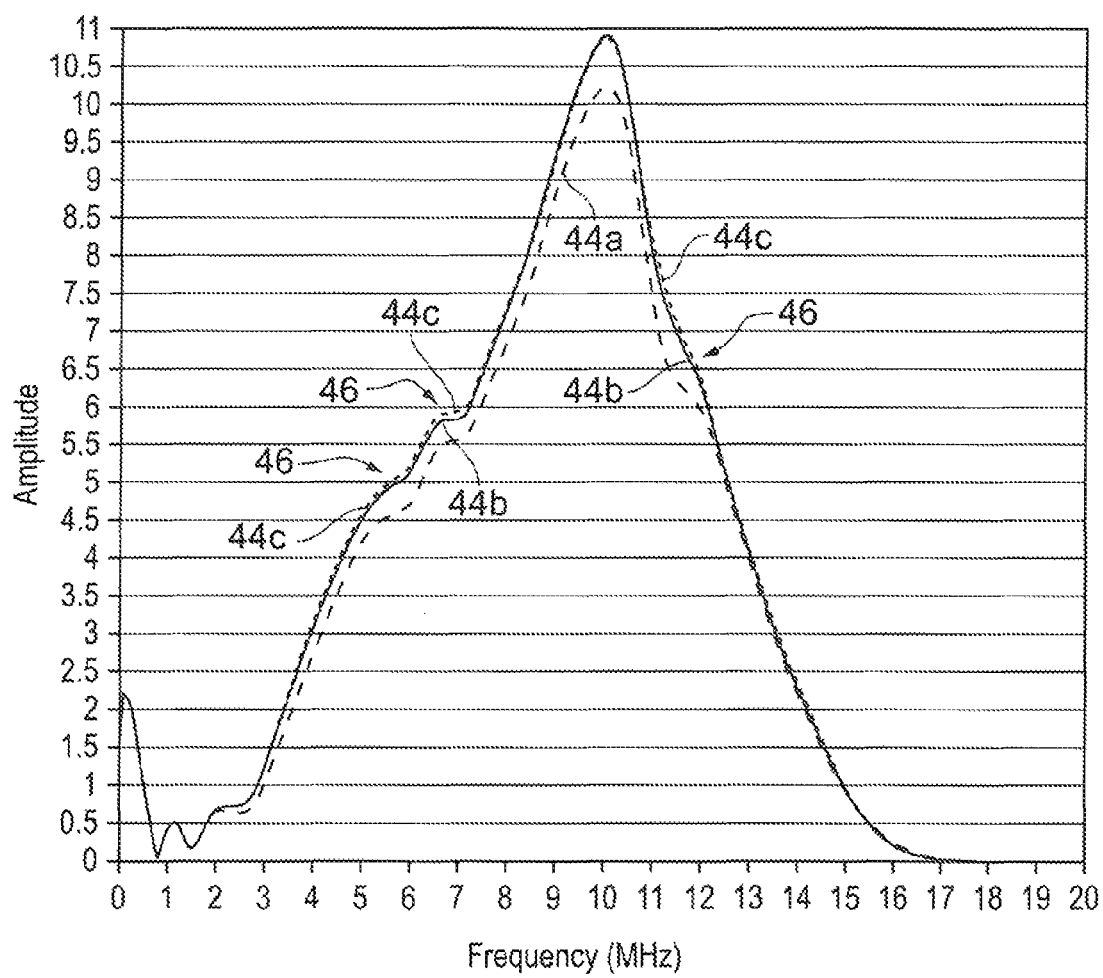

Examples of the present invention will now be described in more detail, by way of example only, and with reference to the accompanying drawings, in which:

FIG. 1 is a simple schematic diagram of ultrasonic measurement apparatus in use to measure an item;

FIGS. 2(a) and (b) illustrate, respectively, an example echo signal received by the apparatus of FIG. 1 when used with a single layer material, and a Fast Fourier Transform (FFT) of the echo;

FIG. 3 is a partial and schematic section through a multi-layer body with associated ultrasonic measurement apparatus;

FIGS. 4(a) and (b) illustrate, respectively, an example echo signal received by the apparatus of FIG. 3, and an FFT of the echo;

FIG. 5 illustrates three pairs of empirical and modelled FFT results from a single item at different stages of wear; and FIG. 6 illustrates FFT results from a single item at different roughness states resulting from wear.

OVERVIEW

FIG. 1 illustrates apparatus 10 for ultrasonic measurement of an item 12. The apparatus 10 comprises a transmitter 14 operable to transmit an ultrasonic signal (indicated at 16) into the item 12. A receiver 18 is operable to receive from the item 12 an echo (indicated at 20) of the transmitted signal 16. The apparatus 10 is operable to measure the frequency spectrum of the echo 20, as will be described, and to make a comparison with another frequency spectrum to extract information relating to a change in the item 12.

In this example, the item 12 is a body of material which, in use, is associated with a second item 13, there being relative motion between the items 12, 13 during use. This results in the possibility of wear at the surface 15. The wear at the surface 15 may result in a change to a dimension of the item 12, as a result of the removal of material, or a change in the roughness of the surface 15.

The transmitter 14 and the receiver 18 are transducers of a type which can inject an ultrasonic signal into the item 12, and receive an echo. For example, the transducers 14, 18 may be piezo-ceramic transducers. In this example, the transducers 14, 18 are bonded to the item 12 in order to ensure a consistent interface between the transducers 14, 18 and the item 12, for reasons which will become apparent. Separate transducers 14, 18 are illustrated in the attached drawings, but it is envisaged that a single transceiver transducer could alternatively be used for both purposes.

The apparatus 10 also includes a data acquisition and processing unit 19. The unit 19 acquires data by generating signals applied to the transceiver 14 to inject an ultrasonic signal into the item 12, and by receiving signals detected by the transceiver 18, representing ultrasonic echoes created in response to the injected signal. The echo signals are processed by the unit 19 in order to extract information relating to a change in the item 12, as will be described. In particular, FFT analysis is used to measure the frequency spectra of echoes, and comparisons are made between spectra, to extract information relating to the item 12. Many different technologies can be used to implement the unit 19. In one example, some or all of the processes which will be described are executed by a general purpose computing device operating under appropriate software control and communicating with the transducers 14, 18 by means of appropriate input and output interfaces (not illustrated separately). In another example, some or all of the processes are executed by dedicated devices. In other examples, a mixture of these approaches is used.

Operation with a Uniform Body

Figure 2B:
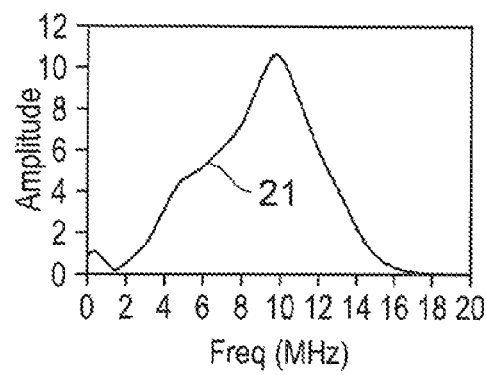

In order to understand the operation of the apparatus 10, it is appropriate first to describe this in relation to an item 12 which consists of a uniform body of a single material, as shown in FIG. 1. In this example, the transmitter 14 is used to inject a short pulse of ultrasound (for example, a pulse of duration of 50 ns at 10 MHz). The shape of the pulse should be reproducible, so that comparisons can be made, as will be described. This pulse of ultrasound forms the signal 16, which propagates across the item 12 as an ultrasonic pressure wave, eventually reflecting from the far side of the item 12, to create an echo 20. The echo 20 propagates back to the receiver 18. FIG. 2a illustrates a typical echo 20 received at the receiver 18 in these circumstances. The Fast Fourier Transform (FFT) of the echo 20 (FIG. 2b) is obtained by the unit 19 and shows that the echo 20 has a significant peak at the frequency (10 MHz) of the signal 16. In this simple example, a time of flight of the signal 16 and the echo 20 can be used to determine the thickness of the item 12.

Operation with a Multi-Layer Body

In many practical situations, the item of interest will not be a simple, uniform body of a single material. Examples include bearings, such as journal bearings. Journal bearings may have a main body of a first material, such as steel, with a working surface of a different material, such as copper. This is illustrated in FIG. 3. A main body 22 of steel has a copper surface layer 24 which provides the working surface 26 of the bearing 28. In use, the working surface 26 will experience wear. Wear may arise as a result of contact (or intermittent contact) with another component, or through erosion, corrosion or abrasion arising from entrained debris. Wear may include dimensional changes by removal of material from the working surface 26, or changes in the roughness of the working surface 26. Lubricant materials will typically be used to reduce or control wear at the working surface 26. The following examples seek to allow information to be extracted relating to changes in the item 28, such as wear.

In this example the apparatus 10 is used to transmit a signal 16 into the main body 22. The signal 16 may again be a short pulse of 10 MHz ultrasound. The signal 16 will propagate through the main body 22 as a pressure wave, until meeting the boundary 30 between the main body 22 and the surface layer 24. (The boundary 30 may be sharply defined or not, according to the techniques used in forming the bearing 28). When the signal 16 encounters the boundary 30, some of the energy will propagate into the surface layer 24 as a signal 32; some of the energy will reflect from the boundary 30 as a first echo 34.

The signal 32 will propagate onward toward the working surface 26. The first echo 34 will propagate back toward the receiver 18. When the signal 32 reaches the working surface 26, it is reflected to create a second echo 36, which propagates back through the surface layer 24 and then through the main body 22, toward the receiver 18. (It is to be noted that the indications of the signals and echoes in the drawings have been simplified in order to achieve clarity, particularly by ignoring the rules by which angles of incidence and reflection will be related in any practical situation).

When the second echo 36 reaches the receiver 18, the total path length travelled is longer than the total path length of the first echo 34 (which has travelled only to the boundary 30, before returning). Consequently, the second echo 36 is delayed in time, relative to the first echo 34. The two echoes 34, 36 form a wave superposition of the corresponding ultrasonic pressure waves and it is this superposition which is detected by the receiver 18.

Figure 4B:
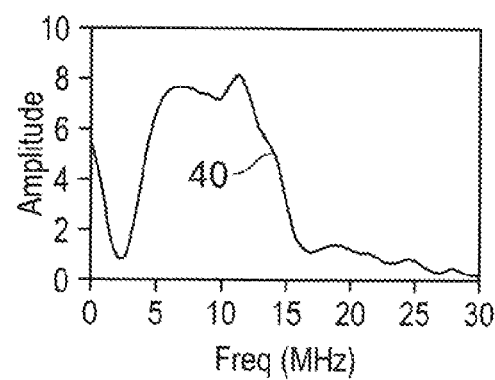

FIG. 4a illustrates a typical echo signal 38 received by the receiver 18 from a two layer system such as that illustrated in FIG. 3. The unit 19 detects the echo signal 38 and processes it by FFT analysis. It can be seen that the echo has a shape which is more complex than the echo received from a uniform body (FIG. 2a), as a result of the superposition of the two echoes 34, 36. Accordingly, the FFT 40 of the echo 38 (FIG. 4b) has a shape which is more complex than the FFT shown in FIG. 2b. The echo 38, and thus the shape of the FFT 40, both contain information about the bearing 28 and can thus be used by the unit 19 to extract information relating to changes in the bearing 28 (particularly wear), as follows.

FIGS. 5a, b and c illustrate the FFT 40 at three stages of wear of the bearing 28. In each of FIGS. 5a, b and c, an empirical FFT 40 is accompanied by a predicted FFT 42 created by mathematical modelling (discussed below). FIG. 5a illustrates the initial condition of the bearing 28. FIG. 5b illustrates the condition after a first amount of wear has occurred, resulting in a reduced thickness for the copper surface layer 24. Further progression of wear results in further reduction of the thickness of the copper surface layer 24, resulting in the condition illustrated in FIG. 5c.

The FFTs 42 are created by mathematical modelling based on a knowledge of the geometry of the bearing 28, and the material properties of the layers 22, 24. This allows predictions and calculations to be made as to the time of flight of the echoes 34, 36 and thus the wave superposition which will arise at the receiver 18 in various conditions of wear. In principle, this type of modelling can be undertaken for systems which are much more complex than the simple bearing 28, and for very many wear conditions.

Considering FIG. 5, it is first to be noted that there are clear differences between the FFTs 40, as the wear progresses. This indicates that the FFTs 40 contain information relating to the changes which are taking place within the bearing 28 and in particular, information about the wear of the copper surface layer 24. It is also to be noted that there is a good correspondence between the shapes of the empirical FFTs 40, and the shapes of the corresponding predicted FFTs 42. Consequently, we have found that wear of the working surface 26 can be monitored by the unit 19 in at least two ways. First, an FFT 40 of an echo 38, representing a measurement of the frequency spectrum of the echo 38, can be compared with another FFT 40, representing another frequency spectrum taken previously. This allows changes in the bearing 28 to be detected and measured. This approach is equivalent to making a comparison between the measured FFTs illustrated at the left of FIG. 5.

Alternatively, an FFT 40 of an echo 38, representing a measurement of the frequency spectrum of the echo 38, can be compared with a predicted FFT 42, representing a predicted frequency spectrum. In practice, this would be achieved by comparing the FFT 42 with a library of predicted FFTs 42, to find the closest match. The actual state of the bearing 28 can then be assumed to correspond with the assumptions from which the closest match FFT 42 was predicted. This approach is equivalent to making a comparison between a measured FFT 40 and the predicted FFTs 42 illustrated at the right of FIG. 5, to find the closest match.

Operation in Relation to Wear and Roughness

The example described above has been described in relation to wear relating to the dimensions of the item. In the following example, the monitored wear relates to roughness at the surface of the item. Changes in roughness take place on a much smaller scale than changes in dimension described above. Changes in the dimension of an item, by wear at the surface, and changes in roughness of the surface, resulting from wear, are both of interest to a tribologist, for example when assessing the effectiveness of a lubrication system.

FIG. 6 illustrates three FFTs 44 obtained from echoes detected in a uniform body of a single material, such as that illustrated in FIG. 1. Accordingly, the shape of the FFTs 44 is generally the same as the FFT shown in FIG. 2. The three FFTs 44 represent different roughness states at the surface from which the transmitted signal 16 is reflected. These different roughness states will be described here as "rough" (FFT 44*a*), "mid" (FFT 44*b*) and "smooth" (FFT 44*c*). Comparison of each of these frequency spectra with the other frequency spectra reveals information about changes in roughness at the surface, as follows.

First, it can be seen that the maximum (peak) amplitude of the rough FFT 44*a* is significantly lower than the maximum amplitude of the mid and smooth FFTs 44*b*, 44*c*. We hypothesise that the rough surface scatters ultrasound much more strongly than the mid or smooth surfaces, so that the amplitude of the echo spectrum at 10 MHz (the frequency of the injected ultrasound pulse) is reduced. As the surface becomes smoother, less scattering takes place, so that more energy at 10 MHz is returned in the echo. This leads to an increased FFT amplitude at 10 MHz. FIG. 6 suggests that comparison of maximum amplitudes can be used to distinguish very rough surfaces from other surfaces, but is less useful for distinguishing between those other surfaces, noting that the maximum amplitude of the mid FFT 44*b* and the smooth FFT 44*c* are substantially the same.

Secondly, it can be seen that the mid FFT (44*b*) and the smooth FFT (44*c*) are very similar in shape and amplitude except at positions 46 part way up the flanks of the spectra. The positions 46 correspond approximately to frequencies 5.5 MHz, 6.5 MHz and 11.5 MHz. We envisage that these differences will provide additional opportunities to distinguish between various roughness conditions.

This second example again shows how the comparison of the measured frequency spectrum with another frequency spectrum (which may be previously measured or previously modelled) can be used to extract information relating to changes in the item, in this case relating to changes in the roughness state of the surface of the item.

This example indicates that the measurements of spectra, described above for monitoring changes in dimension, can also use the same data to monitor changes in roughness.

CONCLUDING COMMENTS

In any of the examples described above, the measured frequency spectra for comparison with another frequency spectrum can be derived as a single (instantaneous) measurement. However, it may be advantageous to make repeated measurements (perhaps a large number, such as 200) to measure a plurality of frequency spectra of echoes, so that these plurality of spectra can be combined for comparison purposes. This allows some averaging or other statistical analysis to be used to improve the data obtained.

It is expected that a large number of repeated measurements can be taken very quickly in comparison with the rate at which wear will occur in any practical situation.

We envisage that the techniques described above can be used in practice to provide real-time measurements of wear in machines, during normal use, allowing improved monitoring, maintenance scheduling and reliability. We envisage that these techniques will be successful across a range of temperatures. However, we envisage that the spectra which are compared should each have been measured at or modelled for substantially the same temperature within the items being measured.

We envisage that these techniques will allow detection of changes at a resolution which depends on the ultrasound frequency used. In general, we expect that the higher the frequency used, the higher the resolution which will be obtained, because of the shorter wavelength.

The techniques make comparisons between measurements made at different times and it is therefore important that the arrangement of the measurement apparatus and the workpiece remains consistent throughout. In particular, we envisage it will be particularly advantageous to use a transducer which is bonded to the workpiece, as described above, for consistency of data.

Many variations and modifications can be made without departing from the scope of the present invention. An ultrasound frequency of 10 MHz has been described; other frequencies could be used. Other arrangements could be used for injecting ultrasound into a workpiece, detecting echoes and measuring and comparing spectra.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

What is claimed is:

1. A method of ultrasonic measurement, the method comprising the steps of:
   causing an ultrasonic signal to be transmitted into a first item;
   causing an echo of the transmitted ultrasonic signal to be received from the first item;
   measuring the frequency spectrum of the echo; and
   determining changes at a surface of the first item resulting from relative motion between the surface of the first item and a second item by undertaking a comparison of the frequency spectrum of the echo with another frequency spectrum to extract information relating to a change in the first item;
   and wherein the said another frequency spectrum is a frequency spectrum measured previously from the same first item.

2. A method according to claim 1, wherein frequency spectra are repeatedly measured for comparison as aforesaid to extract information relating to progressive change in the first item.

3. A method according to claim 1, wherein information is extracted by comparing the shapes of the frequency spectra.

4. A method according to claim 1, wherein the change relates to roughness at the surface of the first item.

5. A method according to claim 4, wherein information is extracted by comparing amplitudes of the frequency spectra.

6. A method according to claim 1, wherein the frequency spectrum of the echo is obtained by an FFT analysis.

7. A method according to claim 1, wherein the steps of transmitting and receiving are repeated to measure a plurality of frequency spectra of echoes, the plurality of spectra being combined for comparison with the said another spectrum.

8. A method according to claim 1, wherein at least one of the first item and the second item is a bearing.

9. A method according to claim 1, where the transmitted signal includes ultrasound at a frequency between 0.5 MHz and 100 MHz.

10. Apparatus according to claim 9, wherein the processor is operable to measure frequency spectra repeatedly for comparison as aforesaid to extract information relating to progressive change in the first item.

11. Apparatus for ultrasonic measurement of a first item, comprising:

a transmitter operable to transmit an ultrasonic signal into the first item;

a receiver operable to receive, from the first item, an echo of the transmitted ultrasonic signal; and a processor operable to measure the frequency spectrum of the echo and to determine changes at a surface of the first item resulting from relative motion between the surface of the first item and a second item by comparing the frequency spectrum of the echo with another frequency spectrum to extract information relating to a change in the first item;

and wherein the said another frequency spectrum is a frequency spectrum measured previously from the same first item.

12. Apparatus according to claim 11, wherein the processor is operable to extract information by at least one of: comparing the shapes of the frequency spectra and comparing amplitudes of the frequency spectra.

13. Apparatus according to any of claim 11, wherein the transmitter is operable to transmit an ultrasound signal which includes a spectrum of frequencies.

14. Apparatus according to claim 11, operable to obtain the frequency spectrum of the echo by an FFT analysis.

15. Apparatus according to any of claim 11, operable to repeat the steps of transmitting and receiving to measure a plurality of frequency spectra of echoes, and further operable to combine the plurality of spectra for comparison with the said another spectrum.

16. Apparatus according to claim 11, wherein at least one of the first item and the second item is a bearing.

17. Apparatus according to any of claim 11, where the transmitter is operable to transmit a signal which includes ultrasound at a frequency between 0.5 MHz and 100 MHz.

\* \* \* \* \*